United States Patent
Govari et al.

(10) Patent No.: US 12,216,179 B2
(45) Date of Patent: Feb. 4, 2025

(54) SAFETY CIRCUIT FOR DC LEAKAGE DETECTION

(71) Applicant: BIOSENSE WEBSTER (ISRAEL) LTD., Yokneam (IL)

(72) Inventors: Assaf Govari, Haifa (IL); Andres Claudio Altmann, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 85 days.

(21) Appl. No.: 17/990,907

(22) Filed: Nov. 21, 2022

(65) Prior Publication Data
US 2023/0221379 A1    Jul. 13, 2023

Related U.S. Application Data

(60) Provisional application No. 63/299,138, filed on Jan. 13, 2022.

(51) Int. Cl.
| | |
|---|---|
| *G01R 31/52* | (2020.01) |
| *A61B 5/00* | (2006.01) |
| *G01K 3/00* | (2006.01) |
| *H02H 3/087* | (2006.01) |
| *H02H 5/04* | (2006.01) |

(52) U.S. Cl.
CPC ............ *G01R 31/52* (2020.01); *A61B 5/6858* (2013.01); *G01K 3/005* (2013.01); *H02H 3/087* (2013.01); *H02H 5/04* (2013.01); *A61B 2560/0276* (2013.01)

(58) Field of Classification Search
CPC .................. G01R 31/52; A61B 5/6858; A61B 2560/0256; H02H 3/087; H02H 5/04
See application file for complete search history.

(56) References Cited

U.S. PATENT DOCUMENTS

| | | | | |
|---|---|---|---|---|
| 3,603,811 | A | * | 9/1971 | Day ...................... A61B 5/276 323/911 |
| 3,886,932 | A | | 6/1975 | Suessmilch |
| 4,572,199 | A | * | 2/1986 | LaCourse ................ A61B 3/14 600/501 |
| 5,995,348 | A | * | 11/1999 | McCartan .............. H02H 9/025 361/45 |
| 9,963,733 | B2 | | 5/2018 | Knopfmacher |
| 2002/0117176 | A1 | * | 8/2002 | Mantzaridis ......... A61B 5/1106 128/204.23 |
| 2013/0314835 | A1 | | 11/2013 | Tseng |

FOREIGN PATENT DOCUMENTS

EP    4212098 B1 *    8/2024    ............. A61B 5/283

OTHER PUBLICATIONS

European Search Report for corresponding EPA No. 23151229.4-1113 dated May 15, 2023.

* cited by examiner

*Primary Examiner* — Paresh Patel

(57) ABSTRACT

A safety circuit, in the form of a switch box, for coupling with a catheter, detects DC leakage or emission from an amplifier circuit of the catheter, and switches a switch to immediately terminates (cuts-off) power to the amplifier circuit. This immediate power termination instantaneously stops DC leakage, which if left unchecked or otherwise undetected, may reach the heart, and disrupt its electrical activity and cause other damage.

15 Claims, 3 Drawing Sheets

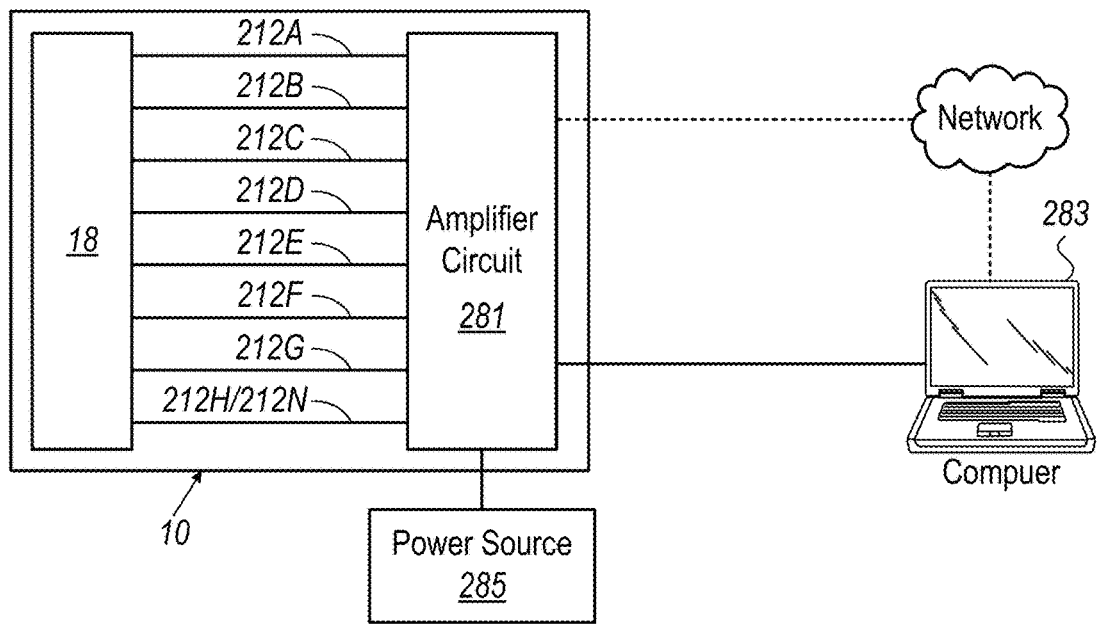
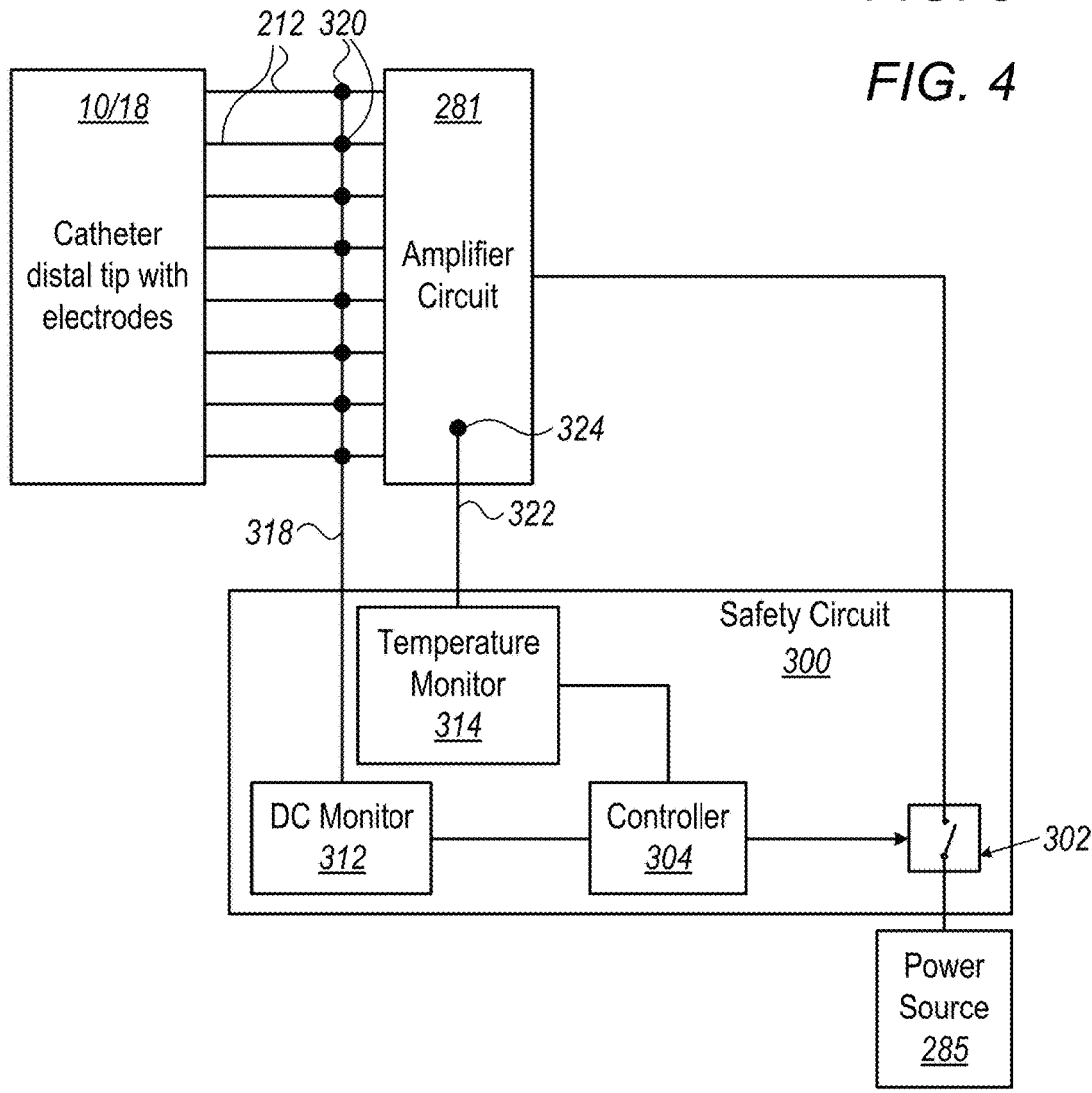
FIG. 3
FIG. 4

SAFETY CIRCUIT FOR DC LEAKAGE DETECTION

CROSS-REFERENCE TO RELATED APPLICATION

This application claims the benefit of U.S. Provisional Patent Application 63/299,138, filed Jan. 13, 2022, which is incorporated herein by reference.

TECHNICAL FIELD

The present disclosure relates generally to medical probes, and particularly to methods and systems for amplifier circuits which receive input current from catheters.

BACKGROUND

Electrophysiology catheters are commonly used for mapping electrical activity in the heart.

BRIEF DESCRIPTION OF THE DRAWINGS

The present disclosed subject matter will be more fully understood from the following detailed description of the examples thereof, taken together with the drawings, where corresponding or like reference numbers or characters indicate corresponding or like elements, in which:

FIG. 3 is a block diagram that schematically illustrates the catheter of FIGS. 1 and 2;

FIG. 4 is a block diagram of the safety circuit of the disclosed subject matter in an exemplary operation with the catheter of FIGS. 1-3; and, FIG. 5 is a flow chart that schematically illustrates an exemplary operational process performed by the safety circuit of FIG. 4, in accordance with an example of the present disclosure.

DETAILED DESCRIPTION OF EXAMPLES

Overview

Electro-Physiological (EP) signals that are acquired by cardiac catheters are typically amplified by suitable amplifiers before they are digitized and processed. One problem arising from such a configuration is DC leakage from an amplifier. Since the amplifier input is connected to an electrode that is inserted into the heart, a DC leakage signal (current or voltage) at the input of the amplifier might reach the heart and disrupt its normal electrical activity or cause damage.

Examples of the disclosed subject matter provide a safety circuit, in the form of a switch box, for detecting DC leakage or emission from an amplifier circuit, and provide for device operational safety. DC leakage may occur from the amplifier circuit aging or malfunctioning. For example, should a DC component reach the infrastructure of a device associated with the amplifier circuit, and ultimately reach the heart, the normal electrical activity of the heart would be disrupted, resulting in damage to the heart.

In some examples, the disclosed safety circuit comprises sensors for detecting leaked DC components from medical probe components, such as amplifier circuits in electrophysiology catheters, that once detected causes a shut off of power to the amplifier circuit, to stop DC leakage. In this manner, DC leakage from an amplifier circuit can be detected and acted upon, resulting in enhanced patient safety.

The disclosed safety circuit provides an alternative to the known bypass circuits that require bulky analog components, for each electrode. As contemporary safety circuits operate on catheters with multiple electrodes, it follows that each electrode would require the bulky analog components, resulting in a large and expensive solution. The present disclosed safety circuit, due to its construction and components, operates on multiple electrodes, and is compact, eliminating the need for the contemporary large and bulky safety circuits.

System Description

Figure 1:
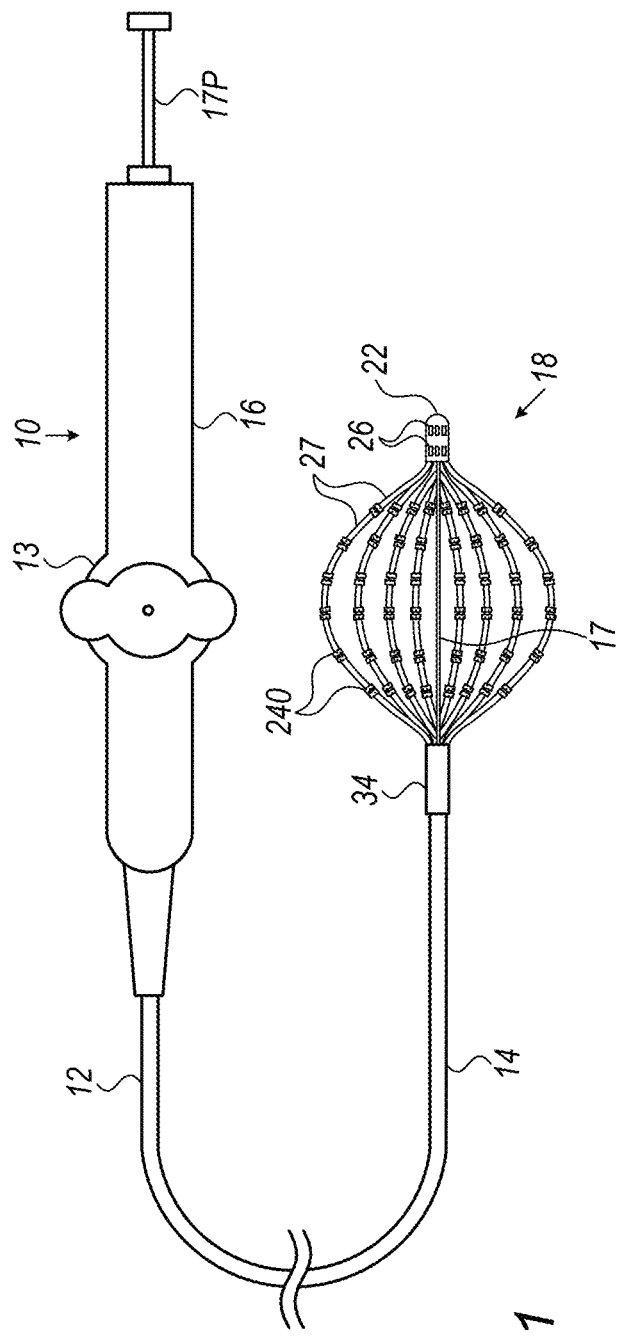
FIG. 1 is a schematic pictorial illustration of a basket catheter system used in an example of a safety circuit of the disclosed subject matter, with the basket portion in an expanded, deployed configuration.

FIG. 1 is a schematic pictorial illustration of catheter 10, also known as a basket catheter or basket electrophysiology catheter, as it includes a basket-shaped high-density electrode assembly 18 for large area mapping, suitable for use with the disclosed safety circuit 300. The basket catheter 10, for example, is in accordance with that disclosed in commonly owned U.S. Pat. No. 9,963,733, entitled: "Basket Catheter With Microelectrode Array Distal Tip", the disclosure of which is incorporated by reference in its entirety herein.

Figure 2:
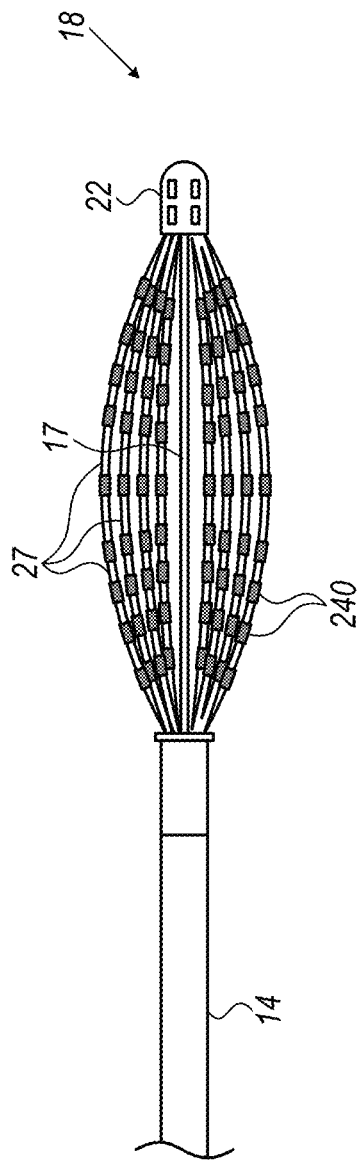
FIG. 2 is a schematic pictorial illustration of the catheter of FIG. 1 with the basket portion in a collapsed configuration.

The catheter 10, with its basket-shaped, high-density electrode assembly 18 provides for large-area mapping, as an integrated distal tip 22 of the electrode 18 provides an array of ultra-high-density microelectrodes for acute focal mapping. The catheter 10 comprises an elongated catheter body 12 having proximal and distal ends, a control handle 16 (including a deflection knob 13 for catheter and basket assembly 18 manipulation) at the proximal end of the catheter body, an intermediate deflection section 14 (of outer tubing 34) distal of the catheter body 12, and the basket-shaped electrode assembly 18 at the distal end of the deflection section 14. The basket-shaped electrode assembly (or "basket assembly") 18 has a plurality of spines 27 whose proximal ends and distal ends surround an elongated expander 17/17P that is afforded longitudinal movement relative to the catheter for adjusting the shape of the basket assembly between an expanded configuration (FIG. 1) and a collapsed configuration (FIG. 2). Mounted on the distal end of the basket assembly 18 is the distal tip 22 having a plurality of surface-embedded microelectrodes 26 whose outer surface is generally flush with the outer surface of the substrate body to present a generally smooth, atraumatic distal tip profile.

Each spine 27 includes one or more ring electrodes 240, which detect electrical activity of heart tissue, to rapidly map a large area of the heart's interior geometry, for diagnosing arrhythmias. Each ring electrode 240 communicates with a corresponding wire 212A to 212N (FIG. 3) (also known as an "electrical line" or "line"), where N represents at least the number of ring electrodes 240 for each spine 27. Hereinafter, the wires 212A-212N are referred to generally as element 212. The wires 212, for example, are packaged in a cable, and the wires 212 communicate with a circuit board in the catheter 10 body.

As shown in FIG. 3, the circuit board serves, for example, as an amplifier circuit 281 (for example, which includes one or more amplifiers (not shown) for each wire (line) 212), which amplifies signals received from the ring electrode 240, and transmits the received signals to a computer 283, external to and in communication with the catheter 10 in a form, e.g., data, understandable by the computer 283. The computer 283 is linked to the catheter 10 either directly (shown in a solid line in FIG. 3) or over a network (shown in broken lines in FIG. 3). The amplifier circuit 281 receives its power from a power source 285.

Detection and Prevention of DC Leakage

FIG. 4 shows a safety circuit 300, also known as a "switch box", in an example operation with a basket catheter, for example, the basket catheter 10, detailed above.

When used with the safety circuit 300, the catheter 10 is modified, such that a switch 302 of the safety circuit 300 is intermediate (e.g., between) the power source 285 and the amplifier circuit 281 of the catheter 10. The switch 302 is, for example, either a hardware switch or a software, or a "soft" switch. The switch 302 communicates with a controller 304. The safety circuit 300 includes, for example, a DC monitor or DC monitoring circuit 312 and a temperature monitor 314, both of which communicate with the controller 304.

The controller 304 communicates with the switch 302, to signal the switch between a first or closed position (hardware switch) or setting (software switch), this first position/setting referred to hereinafter as "first or closed position", where the switch 302 is open or "ON" and power flows from the power source 285 to the amplifier circuit 281, and a second or open position/setting, this second position/setting referred to hereinafter as "second or open position", where the switch 302 is closed or "OFF", and power flow from the power source 285 to the amplifier circuit 281 is cut off, and does not reach the amplifier circuit 281. For example, the first or closed position of the switch 302 is the default position, where power flows from the power source 285 to the amplifier circuit 281 through the switch 302.

For example, the controller 304 is programmable to receive threshold DC currents and/or voltages and threshold temperatures, which when reached or exceeded, cause the controller 304 to signal the switch 302 to move/reset to, or to maintain the second or open position/setting, such that power is cut off to the amplifier circuit 281. This power cut off stops DC leakage and other DC emissions from the amplification circuit 281, such that DC does not flow into the catheter 10 and subsequently reach the heart, and thus, disrupting the normal electrical activity of the heart, and causing damage to the heart.

Typically, the controller 304 comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

A lead 318 extends from the DC monitor 312 to sensors 320, positioned along each of the wires 212. For example, at least one sensor 320 is positioned along each wire (line) 212. The sensors 320 are, for example, DC signal sensors, which detect and/or measure the DC current and/or voltage flowing through the wires 212. The DC current and/or voltage flow, for example, is that typically leaking or otherwise being emitted from the amplifier circuit 281 (e.g., flowing in the direction from the amplifier circuit 281 to the catheter electrode 18). The detected and/or measured DC current and/or voltage is monitored by the DC monitor 312, by obtaining the DC current and/or voltage measured by the sensors 320 (e.g., from DC signals), transmitted by the respective sensor 320 (the transmission being continuous (e.g., instantaneous) or at regular or random intervals, typically in real time), or by the DC monitor 312 polling each respective sensor 320, for example, continuously (e.g., instantaneous) or at regular or random intervals, typically in real time. The sensors 320 can transmit detected and/or measured DC current and/or voltage individually, or together in groups of two or more sensors, and polling may be either of individual sensors 320 at the same or different times, or two or more sensors at the same or different times.

While there is, for example, at least one DC signal sensor 320 per wire 212, with a corresponding lead 318 between the sensor 320 and the DC monitor 312, there may be more than one DC signal sensor 320 per wire 212. For example, multiple sensors 320 for a wire 212 may be on a single or multiple leads 318, the leads 318 extending from the DC monitor 312.

The DC monitor 312 typically reports (e.g., transmits) the presence of the DC signals and/or the measured DC current and/or voltage from the signals (e.g., a value for the measured DC current and/or voltage), obtained from the sensors 320, to the controller 304. This reporting or transmission is, for example, continuous, instantaneous, and in real time. The controller 304 processes the measured DC current and/or voltage from the signals both individually and/or cumulatively, for a given time or given time period.

Should the detected and reported DC current reach or exceed a threshold current and/or voltage (e.g., expressed as a value), for example, either from a current and/or voltage of an individual line 212, or cumulatively, from two or more (at least a plurality) lines 212 at a single time or time period, which is programmed into the controller 304, the controller 304 will signal the switch 302. The signaling of the switch 302 depends on the present position of the switch, whereby the switch 302 moves from the first or closed position to the second or open position, or the switch 302 is maintained in the second or open position, should the switch 302 already be in the second or open position. This instantaneous action allows for the safety circuit 300 to instantly terminate power to the amplifier circuit 281, to stop any harmful effects on the heart from DC leakage to the catheter 10.

For example, a threshold or cutoff for a cumulative DC is 20 µAmps. However, since there may be multiple wires (lines) 212 on a single application specific integrated circuit (ASIC), the threshold may be 2 µAmps for each line 212 of multiple, e.g., sixteen, lines 212 connected to the amplifier circuit 281 (the ASIC) (in FIG. 4, eight lines 212 are shown for convenience of illustration), or alternately, a threshold 1-4 µAmps, to handle cases where the same malfunction, e.g., current leakage, of the silicon effects more than one amplifier, associated with one of the wires (lines) 212. Additionally, should any one of the wires (lines) 212 have a DC above the threshold, the power would be cut off to the amplifier circuit 281.

The temperature monitor 314 includes one or more leads 322 (one shown), each of which communicates with a temperature sensor 324. The temperature sensor(s) 324 are in communication with a location of the amplifier circuit 281, and detect the temperature at the location of the amplifier circuit 281. Each detected temperature is obtained by the temperature monitor 314, which monitors the temperature sensor(s) 324. The monitoring is such that the temperature is obtained, for example, either by the temperature sensor(s) 324 transmitting the temperature to the temperature monitor 314, or the temperature monitor 314 polling the temperature sensor(s) 324. The temperature sensor 324 transmissions or the temperature monitor 314 polling, may be continuous (e.g., instantaneous), or at regular or random intervals, and typically in real time.

The temperature monitor 314 reports (e.g., by transmitting) the detected temperature(s), which were obtained, to the controller 304. This reporting or transmission is, for example, continuous, instantaneous, and in real time.

Should the detected and reported temperature reach or exceed a threshold temperature, for example, which is programmed into the controller 304, the controller 304 will signal the switch 302 to move from the first or closed position to the second or open position, or maintain the switch 302 in the second or open position, should the switch 302 already be in the second or open position. This instantaneous action allows for the safety circuit 300 to instantly terminate power to the amplifier circuit 281, to stop any harmful effects of DC leakage, caused by high temperatures, in the catheter 10.

Figure 5:
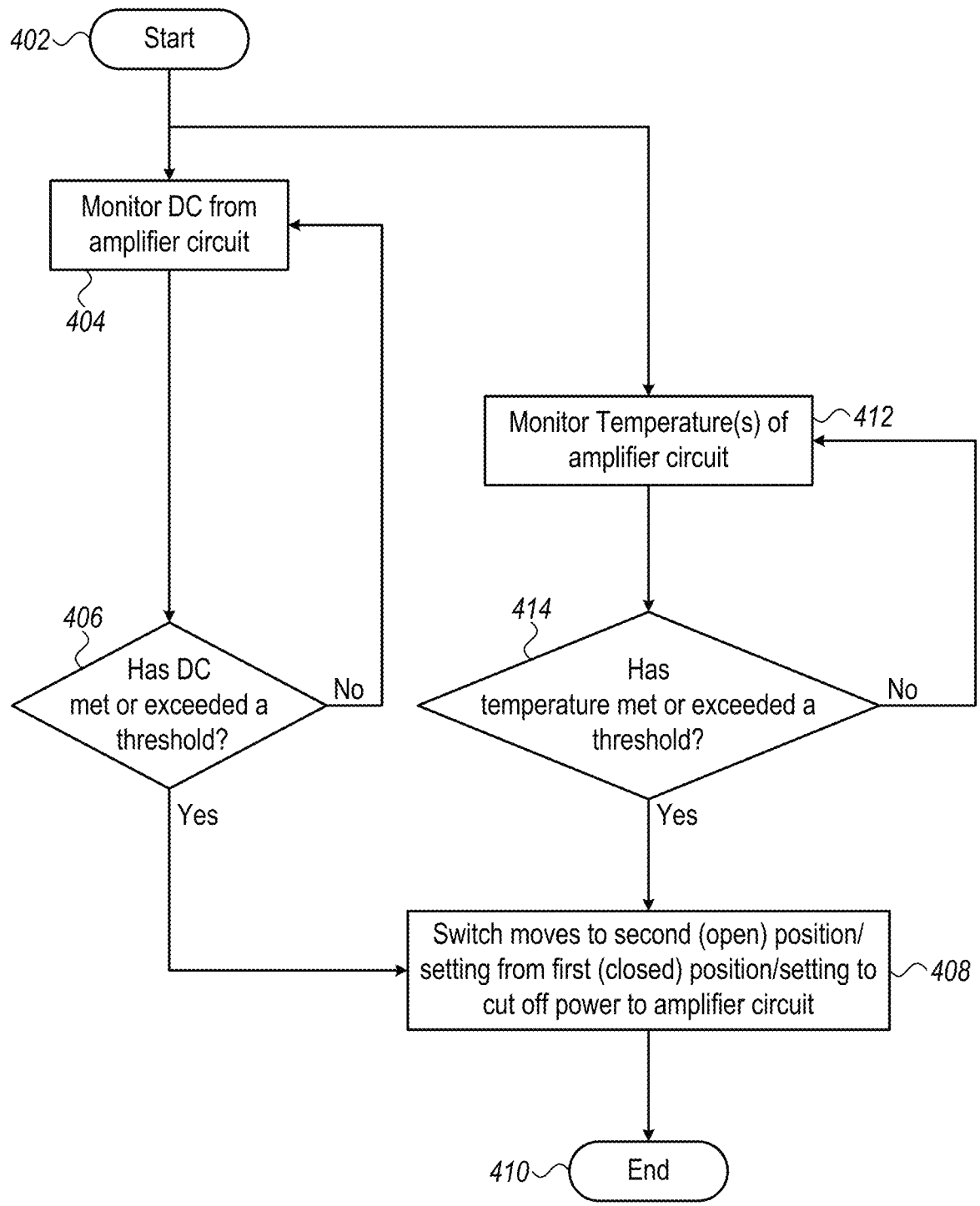

Attention is now directed to FIG. 5, which shows a flow diagram detailing a computer-implemented process in accordance with examples of the disclosed subject matter. The aforementioned process, which includes subprocesses, is performed, for example, by the safety circuit 300, for example, the DC monitor 312, controller 304 and the switch 302, for example, automatically and/or in real time. The process references elements in FIGS. 1-4, as described above.

The process begins at the START block 402. The catheter 10 is operating and the safety circuit 300 is activated, for example, such that the switch 302 is in the first position/setting, where the amplifier circuit 281 receives power from the power source 285.

Moving to block 404, DC signals, including the current and/or voltage associated therewith, from the amplifier circuit 281 are monitored, for example, over the wires 212, via the leads 318, and the respective DC sensors 320, by the DC monitor 312. The process moves to block 406, where it is determined in the controller 304 (which has received the DC data from the DC monitor 312) whether the monitored DC current and/or voltage has met or exceeded a threshold DC current and/or voltage.

If the controller 304 determines that the monitored DC current and/or voltage has not met or exceeded the threshold DC current and/or voltage, the process moves to block 404, from where it resumes.

Alternately, should the controller 304 determine that the monitored DC current and/or voltage has met or exceeded the threshold DC current and/or voltage, the process moves to block 408. At block 408, the controller 304 signals the switch 302 to move/set to the second or open position, where power is cut off to the amplifier circuit 218. This power cut off stops operation of the amplifier circuit 281, stopping any DC leakage or emission from the amplifier circuit 281. The process then moves to block 410 where it ends.

Also, from block 402, and contemporaneous or simultaneous, with the process moving to block 404, the process moves to block 412. At block 412, the temperature monitor 314 monitors one or more locations of the amplifier circuit 281 for temperature (via the temperature sensors 324) and reports (e.g., transmits) the temperatures to the controller 304. The process moves to block 414, where the controller 304 determines whether a threshold temperature has been met or exceeded. If no at block 414, the process moves to block 412, from where it resumes.

If yes at block 414, the process moves to block 408. At block 408, the controller 304 signals the switch 302 to move/set to the second or open position, where power is cut off to the amplifier circuit 281. This power cut off stops operation of the amplifier circuit 281, stopping any DC leakage or emission from the amplifier circuit 281. The process then moves to block 410 where it ends.

While the safety circuit 300 is shown as external to the catheter 10, alternately, the safety circuit 300 may be internal and a part of the catheter 10.

EXAMPLES

Example 1

An apparatus (300) for detecting direct current (DC) leakage from an amplifier circuit (281) coupled to a catheter (10). The apparatus (300) comprises: a switch (302) for controlling the flow of power from a power source (285) to the amplifier circuit (281), the switch (302) comprising a first setting, where power is delivered from the power source (285) to the amplifier circuit (281), and a second setting, where the power from the power source (285) to the amplifier circuit (281) is cut off; a direct current (DC) monitor (312) in communication with the amplifier circuit (281), for monitoring DC signals from the amplifier circuit (281); and, a controller (304) in communication with the DC monitor (312) and the switch (302), the controller (304) for controlling switching of the switch (302) between the first setting and the second setting, in response to the controller (304) determining whether the detected DC signals from the DC monitor (312) have at least met a threshold DC signal.

Example 2

The apparatus of Example 1, wherein the controller (304) additionally controls switching of the switch (302) to change to the second setting from the first setting, or remain at the second setting, when current and/or voltage of the detected DC signals has at least met a threshold current and/or voltage.

Example 3

The apparatus of Example 1 or Example 2, additionally comprising: a temperature monitor (314) in communication with the controller (304), the temperature monitor (314) for monitoring and for obtaining one or more temperatures of the amplifier circuit (281), and for reporting the obtained temperatures to the controller (304), and, should one or more of the reported obtained temperatures at least meet a threshold temperature, the controller (304) causes the switch (302) to: 1) switch from the first setting to the second setting, or, 2) remain at the second setting if the switch (302) is at the second setting.

Example 4

The apparatus of any of Example 1 to Example 3, wherein the controller (304) determining whether the detected DC signals from the DC monitor (312) have at least met a threshold DC signal is based on the DC signals from at least one of the individual lines (212) extending between the catheter (10) and the amplifier circuit (281).

Example 5

The apparatus of any of Example 1 to Example 4, wherein the threshold DC signal comprises a current of 1 µAmp to 4 µAmps.

Example 6

The apparatus of any of Example 1 to Example 5, wherein the controller (304) determining whether the detected DC signals from the DC monitor (312) have at least met a threshold DC signal is based on the cumulative DC signals from at least a plurality of the individual lines (212) extending between the catheter (10) and the amplifier circuit (281).

Example 7

A method for detecting direct current (DC) leakage from an amplifier circuit (281) coupled to a catheter (10). The method comprises: monitoring the amplifier circuit (281) to detect DC signals emitted therefrom; determining whether the detected DC signals at least meet a predetermined threshold current and/or voltage; and, if the current and or voltage from the detected DC signals at least meets the predetermined threshold current and/or voltage, signaling a switch (302) to be at a setting where power from a power source (285) to the amplifier circuit (281) is cut off.

Example 8

The method of Example 7, wherein the amplifier circuit (281) is additionally monitored to detect a temperature of at least one location of the amplifier circuit (218) comprising: determining whether the detected temperature at least meets a predetermined threshold temperature; and, if the detected temperature at least meets the predetermined threshold temperature, signaling a switch (302) to be at a setting where power from a power source (285) to the amplifier circuit (281) is cut off.

Example 9

The method of Example 7 or Example 8, wherein the signaling the switch (302) to be at the setting where power from a power source (285) to the amplifier circuit (281) is cut off, comprises: 1) changing the switch (302) from a closed setting to an open setting, or, 2) maintaining the switch (302) at the open setting if the switch (302) is in the open setting.

Example 10

The method of any one of Example 7 to Example 9, wherein the signaling the switch (302) to be at the setting where power from the power source (285) to the amplifier circuit (281) is cut off, comprises: 1) changing the switch (302) from a closed setting to an open setting, or, 2) maintaining the switch (302) at the open setting if the switch (302) is in the open setting.

Example 11

The method of any one of Example 7 to Example 10, wherein the detected DC signals include DC signals from at least one of the individual lines (212) extending between the catheter (10) and the amplifier circuit (281).

Example 12

The method of any one of Example 7 to Example 11, wherein the detected DC signals include cumulative DC signals from at least a plurality of the individual lines (212) extending between the catheter (10) and the amplifier circuit (281).

Example 13

The method of any of Example 7 to Example 12, wherein the predetermined threshold current is 1 µAmp to 4 µAmps along at least one of the individual lines (212) extending between the catheter (10) and the amplifier circuit (281).

Although the examples described herein mainly address safety circuits and safety monitors for catheters, such as basket catheters, the systems and methods described herein can also be used in other applications, such as with other medical and surgical systems, as well as other systems, and medical probes, where DC leakage or emission is needed to be detected.

The aforementioned disclosed subject matter may, for example, also be in the form of a computer software product. The product comprises, for example, a tangible non-transitory computer-readable medium in which program instructions are stored, which instructions, when read by a processor, cause the processor to detect direct current (DC) leakage from an amplifier circuit of a system such that of a catheter, including basket catheters.

It will thus be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:
1. A system for amplifying signals sensed from each of a plurality of electrodes mounted on a distal end of a catheter, the system comprising:
   an amplifier circuit comprising a plurality of amplifiers, each amplifier coupled to an electrode of the plurality of electrodes and configured for amplifying signals sensed from the electrode with which it is coupled; and
   a safety apparatus configured for detecting at the coupling between the plurality electrodes and the amplifier circuit, direct current (DC) leakage from the amplifier circuit, the safety apparatus comprising:
      a switch for controlling the flow of power from a power source to the amplifier circuit, the switch comprising a first setting, where power is delivered from the power source to the amplifier circuit, and a second setting, where the power from the power source to the amplifier circuit is cut off;
      a direct current (DC) monitor in communication with the amplifier circuit, for monitoring DC signals from the amplifier circuit; and
      a controller in communication with the DC monitor and the switch, the controller for controlling switching of the switch between the first setting and the second setting, in response to the controller determining whether the detected DC signals from the DC monitor have at least met a threshold DC signal.

2. The system of claim 1, wherein the controller additionally controls switching of the switch to change to the second setting from the first setting, or remain at the second setting, when current and/or voltage of the detected DC signals has at least met a threshold current and/or voltage.

3. The system of claim 1, additionally comprising:
a temperature monitor in communication with the controller, the temperature monitor for monitoring and for obtaining one or more temperatures of the amplifier circuit, and for reporting the obtained temperatures to the controller, and, should one or more of the reported obtained temperatures at least meet a threshold temperature, the controller causes the switch to: 1) switch from the first setting to the second setting, or, 2) remain at the second setting if the switch is at the second setting.

4. The system of claim 1, wherein the controller determining whether the detected DC signals from the DC monitor have at least met a threshold DC signal is based on the DC signals from at least one amplifier of the plurality of amplifiers of the amplifier circuit.

5. The system of claim 4, wherein the threshold DC signal comprises a current of 1 μAmp to 4 μAmps.

6. The system of claim 1, wherein the controller determining whether the detected DC signals from the DC monitor have at least met a threshold DC signal is based on a cumulative DC signals from the plurality of amplifiers of the amplifier circuit.

7. The system of claim 1, wherein the controller is configured to switch between the first setting and the second setting, in response to the controller determining that the DC signals from any one of the plurality of amplifiers have at least met a first threshold DC signal or in response to the controller determining that a cumulative DC signals from the plurality of amplifiers have at least met a second threshold DC signal, wherein the second threshold DC signal is greater than the first threshold DC signal.

8. A method for amplifying signals sensed from each of a plurality of electrodes mounted on a distal end of a catheter, the method comprising:
coupling the plurality of electrodes to an amplifier circuit, wherein the amplifier circuit includes a plurality of amplifiers, each amplifier coupled to an electrode of the plurality of electrodes and configured for amplifying signals sensed from the electrode with which it is coupled monitoring direct current (DC) signals from the amplifier circuit at the coupling between the plurality electrodes and the amplifier circuit;
determining whether the detected DC signals at least meet a predetermined threshold current and/or voltage; and
if the current and or voltage from the detected DC signals at least meets the predetermined threshold current and/or voltage, signaling a switch to be at a setting where power from a power source to the amplifier circuit is cut off.

9. The method of claim 8, wherein the amplifier circuit is additionally monitored to detect a temperature of at least one location of the amplifier circuit comprising:
determining whether the detected temperature at least meets a predetermined threshold temperature; and
if the detected temperature at least meets the predetermined threshold temperature, signaling a switch to be at a setting where power from a power source to the amplifier circuit is cut off.

10. The method of claim 8, wherein the signaling the switch to be at the setting where power from a power source to the amplifier circuit is cut off, comprises: 1) changing the switch from a closed setting to an open setting, or, 2) maintaining the switch at the open setting if the switch is in the open setting.

11. The method of claim 9, wherein the signaling the switch to be at the setting where power from the power source to the amplifier circuit is cut off, comprises: 1) changing the switch from a closed setting to an open setting, or, 2) maintaining the switch at the open setting if the switch is in the open setting.

12. The method of claim 8, wherein the detected DC signals include DC signals from at least one amplifier of the amplifier circuit.

13. The method of claim 8, wherein the detected DC signals include cumulative DC signals from the plurality of amplifiers of the amplifier circuit.

14. The method of claim 8, wherein the predetermined threshold current is 1 μAmp to 4 μAmps along at least one amplifier of the amplifier circuit.

15. The method of claim 8, wherein determining whether the detected DC signals at least meet a predetermined threshold current and/or voltage includes determining that the DC signals from any one of the plurality of amplifiers have at least met a first threshold DC signal or determining that a cumulative DC signals from the plurality of amplifiers have at least met a second threshold DC signal, wherein the second threshold DC signal is greater than the first threshold DC signal.

* * * * *